US008349579B2

(12) United States Patent
Raz et al.

(10) Patent No.: US 8,349,579 B2
(45) Date of Patent: Jan. 8, 2013

(54) GALECTIN-3 CLEAVAGE AS A MARKER FOR MATRIX METALLOPROTEINASE ACTIVITY IN CANCER

(75) Inventors: Avraham Raz, West Bloomfield, MI (US); Pratima Nangia-Makker, Troy, MI (US); Rafael Fridman, West Bloomfield, MI (US)

(73) Assignee: Wayne State University, Detroit, MI (US)

( * ) Notice: Subject to any disclaimer, the term of this patent is extended or adjusted under 35 U.S.C. 154(b) by 422 days.

(21) Appl. No.: 12/316,587

(22) Filed: Dec. 11, 2008

(65) Prior Publication Data
US 2009/0269779 A1 Oct. 29, 2009

Related U.S. Application Data

(60) Provisional application No. 61/007,712, filed on Dec. 13, 2007.

(51) Int. Cl.
*C12Q 1/37* (2006.01)
(52) U.S. Cl. ............................................. 435/23; 435/4
(58) Field of Classification Search ................ 435/4, 23
See application file for complete search history.

(56) References Cited

PUBLICATIONS

Ochieng et al. "Galectin-3 is a novel substrate for human matrix metalloproteinases-2 and -9", Biochemistry, 1994, 33:14109-14114.*
Shekhar et al. "Alterations in galectin-3 expression and distribution correlate with breast cancer progression", American Journal of Pathology, 2004, 165(6):1931-1941.*
Toth et al. "Cleavage at the stem region releases an active ectodomain of the membrane type 1 matrix metalloproteinase", Biochem. J. 2005, 387:497-506.*
Nangia-Makker et al. "Galectin-3 cleavage: a novel surrogated marker for matrix metalloproteinase activity in growing breast cancers", Cancer Res., 2007,67(24):11760-11768.*
Ortega et al. "Galectin-3 is a downstream regulator of matrix metalloproteinase-9 function during endochondral bone formation", Molecular Biology of the Cell, 2005, 16:3028-3039.*
Akahani et al., "Galectin-3: A Novel Antiapoptotic Molecule With a Functional BH1 (NWGR) Domain of Bcl-2 Family," *Cancer Res.* 57:5272-6, 1997.
Bergers et al. "Matrix Metalloproteinase-9 Triggers The Angiogenic Switch During Carcinogensis," *Nat. Cell Bio.* 2:737-44, 2000.
Chiappori et al., "A Phase I Pharmacokinetic and Pharmacodynamic Study of S-3304, A Novel Matrix Metalloproteinase Inhibitor, In Patients with Advanced and Refractory Solid Tumors," *Clin. Cancer Res.* 13:2091-9, 2007.

Dumic et al., "Galectin-3: An Open-Ended Story," *Biochem Biophys. Acta.* 1760:616-35, 2006.
Gong et al., "The NH2 Terminus of Galectin-3 Governs Cellular Compartmentalization and Functions in Cancer Cells," *Cancer Res.* 59:6239-45, 1999.
Honjo et al., "Down Regulation of Galectin-3 Suppresses Tumorigenicity of Human Breast Carcinoma Cells," *Clin. Cancer Res.* 7:661-8, 2001.
Itoh et al., "Reduced Angiogenesis and Tumor Progression in Gelatinase A-Deficient Mice," *Cancer Res.* 58:1048-51, 1998.
Levi et al., "Matrix Metalloproteinase 2 Releases Active Soluble Ectodomain of Fibroblast Growth Factor Receptor 1," *Proc. Natl. Acad. Sci. USA* 93:7069-74, 1996.
Nangia-Makker et al., "Galectin-3 Induces Endothelial Cell Morphogenesis and Angiogenesis," *Am. J. Pathol.* 156:899-909, 2000.
Nangia-Makker et al., "The Role of Galectin-3 in Tumor Metastasis," *Lectins and Pathology* 67-77, 2000.
Nangia-Makker et al., "Carbohydrate-Recognition and Angiogenesis," *Cancer and Metastasis Reviews* 19:51-7, 2000.
Nangia-Makker et al., "Induction of Tumorigenicity by Galectin-3 in a Non-Tumorigenic Human Breast Carcinoma Cell Line," *Int. J. Oncol.* 7:1079-87, 1995.
Nelson et al., "Matrix Metalloproteinases: Biologic Activity and Clinical Implications," *J. Clin. Oncol.* 18:1135-49, 2000.
Ochieng et al., "Galectin-3 is a Novel Substrate For Human Matrix Metalloproteinases-2 and -9," *Biochem.* 33:14109-14, 1994.
Ochieng et al., "Modulation of The Biological Functions of Galentin-3 by Matrix Metalloproteinases," *Biochem. Biophys. Acta.* 1379-97-106, 1998.
Olson et al., "Kinetic Analysis of the Binding of Human Matrix Metalloproteinase-2 And -9 to Tissue Inhibitor of Metalloproteinase (TIMP)-1 and TIMP-2," *J. Biol. Chem.* 272-29975-83, 1997.
Shekhar et al., "Alterations in Galectin-3 Expression and Distribution Correlate With Breast Cancer Progression: Functional Analysis of Galectin-3 in Breast Epithelial-Endothelial Interactions," *Am. J. Pathol.* 165:1931-41, 2004.
Stuelten et al., "Breast Cancer Cells Induce Stromal Fibroblasts to Express MMP-9 Via Secretion of TNF-Alpha and TGF-Beta," *J. Cell Sci.* 118-2143-53, 2005.
Van de Wiele et al., "Imaging Probes Targeting Matrix Metalloproteinases," *Cancer Biother. Radiopharm.* 21:409-17, 2006.
Wright et al., "Cigarette Smoke Upregulates Pulmonary Vascular Matrix Metalloproteinases Via TNT-Alpha Signaling," *Am. J. Physiol. Lung Cell Mol. Physiol.* 292:L 125-33, 2007.

\* cited by examiner

*Primary Examiner* — Susan Hanley
*Assistant Examiner* — Bin Shen
(74) *Attorney, Agent, or Firm* — C. Rachal Winger (57) ABSTRACT

Provided are differential antibodies recognizing the cleaved and non-cleaved forms of matrix metalloproteinases (MMPs), and methods of using the antibodies as surrogate diagnostic markers for the presence of active MMPs in cancer, such as growing breast cancers.

6 Claims, 7 Drawing Sheets
(5 of 7 Drawing Sheet(s) Filed in Color)

GALECTIN-3 CLEAVAGE AS A MARKER FOR MATRIX METALLOPROTEINASE ACTIVITY IN CANCER

This application claims priority to U.S. Provisional Application Ser. No. 61/007,712 filed Dec. 13, 2007, the entire contents of which are incorporated by reference herein.

STATEMENT REGARDING FEDERALLY SPONSORED RESEARCH

This work was funded by National Institute of Health Grants R37CA46120-19, RO1 CA-61986-11, and RO1 CA100475, and the United States government has, therefore, certain rights to the present invention.

TECHNICAL FIELD

Background of the Invention

Matrix metalloproteinases (MMPs) are a family of Zn-dependent proteinases that can be divided into 5 groups based on substrate specificity. They remodel extra-cellular matrix (ECM) components and cleave a broad range of cell surface proteins resulting in substrate degradation in areas of cell-matrix contact, thus affecting various cellular activities. Certain aspects of MMPs involvement in tumor metastasis such as angiogenesis, invasion, and establishment of metastatic foci, have received extensive attention resulting in data concerning critical roles of MMPs in cancer (1). The gelatinases MMP-2 and -9, which specifically degrade collagen IV, are important for initiation and development of tumor vascularization (2, 3).

Failed therapies directed against MMPs in cancer patients may be attributed, in part, to lack of diagnostic tools to differentiate between pro- and active MMPS, which indicate whether a treatment is efficacious or not. There is a need in the art for materials and methods to distinguish between pro-MMPs and active MMPs. Galectin-3 is cleavable in vitro by MMPs. This invention helps to fulfill the need by providing differential antibodies recognizing cleaved and non-cleaved forms of galectin-3, and demonstrating their clinical utilization as a surrogate diagnostic marker for the presence of active MMPs in cancer, such as growing breast cancers.

SUMMARY OF THE INVENTION

The disclosure provides anti-MMP-2/9 and anti-galectin-3 monoclonal and polyclonal antibodies useful for visualizing cleaved galectin-3 in tissues such as patient samples.

Also provided are simple, rapid and reliable surrogate markers for MMPs' activities in cancer, including growing breast cancers.

Further provided are methods of inhibiting tumor angiogenesis by targeting MMPs using synthetic MMP inhibitors.

The present invention has industrial applicability and is advantageous in the clinical setting to identify whether MMP is cleaved or uncleaved in patient samples, thereby assisting in determining which tumors are amenable to treatment with inhibitors of specific MMPs.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1.

FIGS. 2A and B.

FIG. 3. FIG. 3(I)A-D shows angiogenesis in the xenografts: The sections were stained with anti-CD34 to identify the blood vessels. Top left: Vector; Top right: 11-9-1-4; Bottom left: M33; Bottom right: M33+64. Arrows indicate positive staining. Bar: 200 micron. FIG. 3(II)A-D shows TUNEL assay in the xenografts: Top left: Vector; Top right: 11-9-1-4; Bottom left: M33; Bottom right: M33+64. Green color represents the apoptotic nuclei. Bar: 100 micron FIG. 4.

FIG. 5.

FIG. 6.

DETAILED DESCRIPTION OF THE INVENTION

According to the present disclosure, wild type and cleavage resistant galectin-3 were constructed and expressed in galectin-3 null human breast carcinoma cells (BT-549). Tumorigenic and angiogenic potential of the clones was studied by injections into nude mice. MMP-2, -9, full length and cleaved galectin-3 were localized in the xenografts by immunohistochemical analysis of paraffin embedded sections using specific antibodies. Activities of MMP-2/9 were corroborated by in situ zymography on frozen tissue sections.

Galectin-3 cleavage was demonstrated in vivo by differential antibody staining and co-localized with predicted active MMPs both in mouse xenografts and human breast cancer specimens. In situ zymography validated these results. In addition, BT-549 cells harboring non-cleavable galectin-3 demonstrated reduced tumor growth and angiogenesis as compared with the wild type.

The results of the Examples below indicate that galectin-3 cleavage is an active process during tumor progression and can be used as a simple, rapid and reliable surrogate marker for MMPs' activities in growing breast cancers. Without being bound by a specific mechanism, the results indicate that dependency of tumor angiogenesis on the activity of these MMPs renders this step a likely target of synthetic MMP inhibitors.

The search for MMP inhibitors with possible anti-cancer efficacy is a nearly three-decade endeavor and an ideal effective inhibitor is yet to be found (Reviewed by (4, 5). Possible reason(s) for this failure include broad MMP sub-type selectivity and toxicity as well as the diversity of MMP biology. MMPs have been shown to enhance angiogenesis by recruiting pericytes (6), releasing ECM bound angiogenic growth factors (7), exposing cryptic pro-angiogenic integrins binding sites (8, 9), and cleaving endothelial cell-cell adhesion molecules (8, 10). MMPs can also contribute negatively to angiogenesis through the generation of endogenous angiogenesis inhibitors by proteolytic cleavage of collagen and plasminogen and by modulating cell receptor signaling by cleaving off their ligand-binding domains (11, 12). MMPs are synthesized as inactive pro-enzymes, which are activated by proteolytic cleavage of the pro-peptide domain (13).

However, to date, there is no simple diagnostic tool to distinguish between active and non-active MMPs in vivo. To search for an anti-cancer inhibitor, which must possess selectivity against the MMP subtype critically important in relation to temporal progression of metastasis as well as with degradation of the matrix, a foremost requirement is to be able to differentiate between the active and the proactive form of MMP in the tissue. Two techniques are currently being used to evaluate MMP activity in tumors: MMP targeting probes for in vivo imaging (14) and in situ zymography (15-17). The results obtained from in vivo imaging have yet to be validated by biochemical or functional methodologies (14).

In situ zymography is difficult to analyze due to imprecise localization, broad range of targets and need of adequate controls to validate specificity and efficacy. Moreover, it is only applicable to fresh frozen specimens. The present disclosure provides evidence that cleavage of galectin-3 can be used as a novel surrogate diagnostic marker for the activity of MMP-2/9 in cancer tissues, which can be easily analyzed by differential immuno-staining on paraffin-embedded specimens as well as fresh frozen sections, providing a wider range and ease of use.

Galectin-3, a ~30 kDa chimera carbohydrate-binding protein belonging to the galectin gene family, is composed of three distinct structural motifs, an amino terminal domain consisting of 12 amino acid residues, preceding an amino terminal half of collagen-like sequence containing Pro-Gly-Tyr tandem repeats, and a sugar-binding carboxy terminal half (18-20). The collagen-like domain of galectin-3 is susceptible to rapid and efficient cleavage by MMPs (enzyme/substrate 1/10-100) in particular MMP-2, MMP-9 and MT1-MMP at the $Ala^{62}$-$Tyr^{63}$ peptide bond, resulting in the generation of a ~22 kDa cleaved product (19).

Although the N-terminal region of human galectin-3 contains five Ala-Tyr repeats, the $Ala^{62}$-$Tyr^{63}$ peptide bond is the only site that is sensitive to MMP-2/9 cleavage (19). The $Ala^{62}$-$Tyr^{63}$ is followed by histidine whereas the other sites are followed by proline. This suggests that structure around the MMP cleavage site may be important in determining its availability for enzymatic degradation. Galectin-3 is implicated in different cell lineages at different developmental and pathological stages and is involved in cell growth, apoptosis resistance, adhesion, differentiation, inflammation, transformation, angiogenesis, invasion and metastasis (21, 22).

Galectin-3, although present in the cytoplasm, nucleus and the cell surface, is also secreted into the extra-cellular matrix, where it binds to the ECM proteins laminin, fibronectin and collagen IV. An additional band of ~22 kDa was observed in the cell lysates and a ~27 kDa from the conditioned medium from the three-dimensional co-cultures of epithelial and endothelial cells (23). The 22 kDa polypeptide is also observed in the conditioned medium from various cell lines occasionally.

This disclosure shows, for the first time, the cleavage of galectin-3 by MMPs in vivo and its co-localization with active MMPs. This discovery has industrial applicability in that it will assist in monitoring MMP activity in cancer tissues and in predicting the efficacy of MMP inhibitors in vivo. In addition, the approach described here may aid in the diagnosis and prognosis of the diseases involving MMP activity due to its ease of use, reliability and cost effectiveness.

The strong causal relationship between MMPs over-expression and a wide range of tumorigenic events, including early carcinogenesis, tumor growth, tumor invasion, angiogenesis and metastasis, makes them attractive therapeutic targets. Consequently, several broad range inhibitors (MMPI) advanced to phase III clinical trials in patients with advanced cancer. Unfortunately, the trials failed to reach their end points of increased survival (5, 30, 31), probably due to lack of adequate target validation and identification of in vivo substrate(s), among other factors. Indeed, to date, no diagnostic marker is available in the prior art to distinguish between latent and active MMP(s) to monitor tumor MMPs' response to treatment.

The results disclosed herein demonstrate that cleaved galectin-3 co-localized with active MMP-2 and MMP-9 and therefore, can be used as a novel diagnostic marker for MMP activity. In paraffin embedded DCIS.com xenograft, epithelial cells stained for intact galectin-3, while the stromal cells stained only for cleaved galectin-3, where it is localized following its secretion and cleavage. The results were validated using in situ zymography on fresh frozen tissue. Whereas total MMP-2/9 showed positive staining in epithelial and stromal cells, the active MMPs were identified only in the stroma by in situ zymography and co-localized with cleaved galectin-3 attesting to the validity of the use of galectin-3 cleavage as a surrogate marker for MMPs activities.

The localization of MMP activity in the stroma of the xenografts confirms the earlier observation of Stuelton et al in CA1A xenografts and co-cultures of fibroblasts and CA1A cells (17). The differential staining of full length versus cleaved galectin-3 could also predict the activity of MMP in human DCIS and infiltrating ductal carcinoma. Many cells adjacent to the stroma exhibited the presence of cleaved galectin-3 and probably active MMP-2 and -9 in DCIS indicating their possible invasive phenotype. Consistent with this observation, the invasive cell clusters and stroma were positive for cleaved galectin-3 and active MMP-9 in the infilterating ductal carcinoma, whereas the ductules that maintained a normal morphology expressed only full-length protein detected by monoclonal as well polyclonal anti-galectin-3 antibodies.

The diverse effects of MMP-2 and -9 cleavage on many proteins have been reported, e.g. MMP-9 cleaves the pro-angiogenic cytokine IL-8, increasing its activity ten-fold, as well as degrading and inactivating the angiogenic inhibitor platelet factor-4 (32). On the other hand, MMP-2 cleaves the FGF receptor 1 (FGFR1), releasing the soluble ectodomain of FGFR1 that can still bind FGFs, but lacks signaling capacity (33). Proteolytic processing of some ECM substrates such as laminin 5 exposes cryptic epitopes (34, 35) and new molecules with properties that are distinct from their precursor protein (36). In vitro cleavage of galectin-3 by MMP-2/-9 resulting in a ~22 kDa product has been reported, but its occurrence in vivo, and its biological significance had not been elucidated.

It was reported that loss of its N-terminus 62 amino acids leads to increased binding of the ~22 kDa fragment to endothelial cells (23) and laminin (26). Injection of the cleaved galectin-3 peptide containing 108-250 amino acids into mice bearing MDA-MB-435 tumors resulted in loss of tumor growth and metastasis because of competitive inhibition of carbohydrate binding (37). It was suggested that loss of the N-terminus reduces self association of galectin-3 and thereby abrogates the biological properties dependent on such association e.g. formation of tumor cell emboli in vivo and hemagglutination in vitro (26). Yang et. al., however showed that only the C-terminus of galectin-3 could self-associate in the absence of its saccharide ligand (38), raising more questions about role of the collagen-like domain in galectin-3 and how its interaction with MMP-2/-9 affects biological functions of galectin-3. To answer these questions, we created cleavage resistant galectin-3. The mutations rendered the recombinant protein resistant to cleavage at that particular site, but the protein cleaved at the remaining site.

Single or double mutations at the MMP cleavage sites did not alter cellular distribution of galectin-3, but inhibited its secretion. Intracellular galectin-3 regulates pathways including mRNA splicing reactions, cell growth, cell cycle and apoptosis (38-41), while extra-cellular galectin-3 modulates cellular adhesion and signaling, immune response, angiogenesis and tumorigenesis (21, 42-46) by binding to cell surface glycoproteins such as integrin subunits (12, 26) or to extra-cellular matrix glycoproteins such as laminin, fibronectin and collagen IV (21, 47).

We have shown earlier that over-expression of galectin-3 in non-tumorigenic breast or colon cancer cell lines induced tumorigenicity and metastasis, whereas its suppression resulted in loss of tumorigenicity and metastasis (24, 48, 49). When the clones were injected in nude mice, the wild type clone showed a rapid increase in tumor volume over 35 days, but cleavage resistant clones or vector transfected cell clones showed a significantly low tumor take and tumor growth.

The galectin-3 mutant clones showed lack of angiogenesis and induction of apoptosis in the xenografts. It was proposed earlier that secreted galectin-3 binds to cell surface receptors on endothelial cells inducing their migration and morphogenesis leading to angiogenesis (50). Absence of secreted protein in the mutated clones may be the reason for inability of these cells to induce blood vessel formation. The xenografts from cleavage resistant cells also showed many more apoptotic cells compared to BT-549 11-9-1-4 cells.

Even though the cellular localization of galectin-3 was not affected in mutant clones, on the cell surface however, the mutant proteins could not be cleaved and affect processes like chemo-invasion, chemotaxis, tumor growth and angiogenesis. It is possible that the cleaved fragment is responsible for the tumorigenic potential of the cells. Once the surface protein is cleaved, the carbohydrate binding domain remains attached to the surface receptor, and the cleaved product is released into the extra-cellular matrix, where it may either interact with other extra-cellular proteins or may be internalized and interact with various signal transduction pathways.

In summary, the disclosure indicates that galectin-3 is cleaved in vivo by MMPs and this phenomenon can be used to distinguish between active and latent MMPs in the tumor, which could affect decisions regarding therapeutic strategies and anti-MMP drugs efficacy.

It should be understood that the Examples and embodiments described herein are for illustrative purposes only and that various modifications or changes in light thereof will be suggested to persons skilled in the art and are to be included within the spirit and purview of this application.

EXAMPLES

Example 1

Materials and Methods

Cell Lines, Antibodies and Recombinant Enzymes. The human breast cancer cell line BT-549 was obtained from Dr. Eric W. Thompson (St. Vincent's Institute of Medical Research and University of Melbourne, Melbourne, Australia). The cells were maintained in Dulbecco's Minimal Essential Medium (Invitrogen Corporation, Carlsbad, Calif.) containing 10% fetal calf serum, essential and non-essential amino acids (Invitrogen), vitamins, and antibiotics (Mediatech Cellgro Inc., Herndon, Va.). 11-9-1-4 is a clone obtained by the transfection of wild type galectin-3 in BT-549 as described earlier (24). MCF10DCIS.com cells were developed at the Karmanos Cancer Institute (25) and maintained in DMEM/F12 (1:1) with 5% horse serum, 0.029M sodium bicarbonate, and 10 mM HEPES. All cells were maintained in a humidified chamber with 95% air and 5% $CO_2$ at 37° C.

The cells were grown to near confluence and detached from the monolayer with 0.25% trypsin and 2 mM EDTA for 1-2 min at 37° C. A monoclonal antibody specific for full-length galectin-3 was isolated from the hybridoma TIB166 clone (ATCC, Manassas, Va.). A polyclonal antibody (anti-hL31) was prepared against the whole molecule, which recognized the full length as well as fragments of galectin-3 (19, 26). Human recombinant pro-MMP-2 and pro-MMP-9 were expressed in HeLa cells infected with the appropriate recombinant vaccinia viruses and purified to homogeneity, as previously described (27). The zymogen were activated by incubation with 1 mM p-aminophenylmercuric acetate (APMA) in a buffer containing 0.02% Brij-35, 5 mM Tris HCl pH 7.5, 0.15 mM NaCl, 5 mM $CaCl_2$ at 37° C. for 30 min. Anti-CD34 antibodies were from Cell Sciences (Canton, Mass.). Anti matrix-metalloprotease-9 and 2 antibodies were from Oncogene (Cambridge, Mass.).

Site Directed Mutagenesis. To generate various point mutations on galectin-3 human cDNA, Quick Change Site Directed Mutagenesis Kit (Strategene, LaJolla, Calif.) was employed using the primer pairs sense 5'-CTGCTGGGG-GAGGGGGCTACCCAGG-3' (SEQ ID NO:1) and antisense 5'-CCTGGGTAGCCCCCTCCCCCAGCAG-3' (SEQ ID NO:2) for A33G; and sense 5'-GCGCCTACCCTGGAG- CACCTGGAGC-3' (SEQ ID NO:3) and antisense 5'-GCTC-CAGGTGCTCCAGGGTAGGCGC-3' (SEQ ID NO:4) for H64P. Briefly, pGEX-6P-2 vector containing human wild type galectin-3 cDNA fused with Glutathione-S-transferase (GST) was used as a template for PCR to generate A33G and H64P point mutations. After amplification, the template DNA was cleaved with Dpn-1 restriction enzyme and transformed into Escherichia coli (E. coli) XL1-Blue super-competent cells. Recombinant pGEX-6P-2/gal-3 mutant plasmids were purified and sequenced at the Macromolecular Core Facility of Wayne Sate University. Double mutations including both A33G and H64P were generated using the A64P primer pair on plasmid containing the A33G mutation.

Protein Purification and Cleavage by MMP-2 and -9. The mutant and wild type galectin-3 proteins were isolated as GST fusion proteins using the manufacturer's instructions (GE Healthcare Biosciences Corp., Piscataway, N.J.). Briefly, E. coli containing the desired plasmid were grown to log phase and protein expression was induced by adding 0.1 mM IPTG. After 4 hr, the bacteria were centrifuged and the pellet was sonicated in 1×PBS. After solubilization of the proteins with 1% Triton X-100, the extract was centrifuged and the supernatant was incubated with slurry of Glutathione Sepharose 4B with gentle agitation to bind the fusion protein to the slurry. Galectin-3 was separated from the fusion protein by incubation with Prescission Protease (GE Healthcare Biosciences Corp.) and isolated by centrifugation.

The purified protein was incubated with activated recombinant MMP-2 and MMP-9 at a molar ratio of 1:10 for 30 min and separated on a 12.5% polyacrylamide gel and analyzed by Western blot analysis using polyclonal anti-galectin-3 antibodies to detect full length as well as cleaved fractions of galectin-3.

Stable Transfection of Galectin-3 Mutants. To analyze the biological significance of these substitutions in the context of galectin-3 mediated functions, the coding sequence of galectin-3 containing mutations at A33G, H64P and A33G/H64P was removed from the pGEX-6P-2 vector by restriction digestion and placed into pCNC10 expression plasmid containing the cytomegalovirus early promoter and a dominant selection marker, G418 (24). The orientation of the insert was determined by restriction mapping and transfected in the non-galectin-3 expressing non-tumorigenic breast cancer cell line BT-459 with either the control (pCNC10 vector) or the pCNC10-mutated galectin-3 construct by LipofectAMINE reagent (Life Technologies Inc., Gaithersburg, Md.) according to the manufacturer's protocol.

After 48 hr, 500 µg/ml G418 (Invitrogen, Carlsbad, Calif.) was added to the cultures for 14 days to obtain stable transfected clones. Single cell clones were expanded and galectin-3 expression was determined by Western blot analysis. From each transfection, the clone with highest galectin-3 expression was selected. The resulting clones were given the nomenclature of M33, M64, M33+64, vector and 11-9-1-4 for A33G+H64P, A33G+H64P, vector alone and wild type galectin-3 transfections respectively.

Western Blot Analysis. $1 \times 10^6$ cells were seeded in 100 mm petri dishes. The cells were trypsinized, lysed and equivalent numbers of cells ($1 \times 10^5$) or equal amounts of total protein were subjected to SDS-PAGE and Western blot analysis with a 1:500 dilution of TIB166 or 1:2000 dilution of anti-galectin-3 polyclonal antibody. Blots were also immunoreacted with a 1:5000 dilution of anti-tubulin mouse polyclonal antibody (Santa Cruz Biotechnology Inc., Santa Cruz, Calif.) to normalize for variation in protein loading.

Tumor Growth in Nude Mice. $2 \times 10^6$ cells suspended in Matrigel were injected into NCR nu/nu mice, obtained from Taconic (Germantown, N.Y.) into the mammary fat pad region subcutaneously on both sides in two groups of 6 mice each, respectively. Tumor growth was measured twice a week and the tumor volumes were calculated using the formula: volume=length×width×width/2. The xenografts were harvested at 35 or 56 days as described. The tumors were weighed, fixed with 10% buffered formalin, and processed for immunohistochemical staining. As the BT-549 cells transfected with galectin-3 formed undifferentiated tumors in nude mice, MCF10 DCIS.com xenografts and human DCIS were used to analyze if differential distribution of galectin-3 could also be detected in differentiated tumors.

The DCIS xenografts were obtained similarly by injecting MCF10 DCIS.com cells (25, 28). After 28 days the xenografts were harvested, half of the tumor was fixed with buffered formalin, while the other half was fixed with 2-methylbutane in liquid nitrogen. The human DCIS serial sections were obtained from Karmanos Cancer Institute tissue core. The infiltrating ductal carcinoma sections were part of a breast cancer progression tissue array (BR480) from U.S. Biomax (Rockville, Md.).

In situ Zymography. In situ zymography was performed on the fresh frozen DCIS xenografts as described by Mook et. al. (29). In brief, 8 micron thick cryosections were air dried, rehydrated with PBS for 5 min and overlaid with a solution of 50 µg/ml fluorescein-labeled gelatin (DQ gelatin; Molecular Probes, Eugene, Oreg.), 1% w/v low melting temperature agarose (BioWhittaker Molecular Applications, Rockland, Me.) and 5 µg/ml DAPI (Molecular Probes) in PBS in the presence or absence of 2 mM EDTA and incubated on ice for 15 min followed by incubation in a humidified chamber at 37° C. for 2 hr. Protease catalyzed hydrolysis of the heavily labeled and totally quenched DQ Gelatin relieved the intramolecular self quenching, yielding brightly fluorescent peptide, which was visualized by using imaging microscope.

Immunohistochemical Analysis. Four µm tissue sections were deparafinized, rehydrated and microwaved on high 2 times for 5 min each in 1 mM sodium citrate buffer, pH 6.0. The sections were washed three times in PBS and blocked with Super Block (Skytek Laboratories, Logan, Utah) for 10 min. Sequential sections were incubated with primary antibodies (anti-CD34, anti-galectin-3 monoclonal, anti-galectin-3 polyclonal, and anti MMP-2 and -9) at 4° C. overnight at the suitable dilution. The sections were washed 3 times for 10 min each in PBS and linked with the appropriate host secondary antibodies (Vector Laboratories, Burlingame, Calif.). The secondary antibodies were tagged with Avidin biotinylated horseradish peroxidase, colorized with 3'-3'-diaminobenzidine and counterstained with hematoxylin. Visualization and documentation were accomplished with an OLYMPUS BX40 microscope supporting a Sony DXC-979MD 3CCCD video camera and stored with the M5+ micro-computer imaging device (Interfocus, Cambridge, UK).

TUNEL Assay. TdT mediated dUTP Nick End Labeling (TUNEL) assay was performed to visualize the fragmented DNA directly by fluorescence microscopy in paraffin embedded sections using DeadEnd Fluorometric TUNEL system (Promega, Madison, Wis.). Briefly, the paraffin sections were deparafinized and permeabilized with proteinase K. Fluorescein 12-dUTP was then catalytically incorporated into the 3'-hydroxyl ends, which are exposed in fragmented DNA of the apoptotic cells using the enzyme terminal deoxynucleotidyl transferase (TdT). The sections were then counterstained with propidium iodide, which, in contrast to fluorescein-12-UTP stains both apoptotic and non-apoptotic cells.

Statistical Analysis. The experiments conducted to measure growth of the tumors were repeated twice with multiple animals. We used one-way ANOVA with Tukey's multiple comparison test to calculate the statistical significance when the number of readings was the same and Dunnett's multiple comparison test using Prism software in the experiments where the number of readings was not the same. All statistical tests were two sided, and p values less than 0.05 were considered statistically significant.

Example 2

Cleavage of Galectin-3 Mutants by MMP-2 and -9

First we identified the amino acids that were important in determining the susceptibility of galectin-3 to MMPs cleavage and mutated them. Five galectin-3 mutants A63G, A62V, Y63H, Y63P and H64P were generated by amino acid substitution around the MMP cleavage site. Only the two mutants Y63P and H64P showed resistance to cleavage at the $Ala^{62}$-$Tyr^{63}$ site, while exposing a new cleavage site producing a ~27-kDa polypeptide. N-terminal sequencing revealed that the 27-kDa product displays an N-terminus starting with $Ala^{33}$ indicating that the alternate cleavage site occurs at the $Gly^{32}$-$Ala^{33}$ peptide bond. We performed amino acid substitutions at this new site and obtained clones displaying A33G or H64P substitutions alone or in combination.

Figure 1:
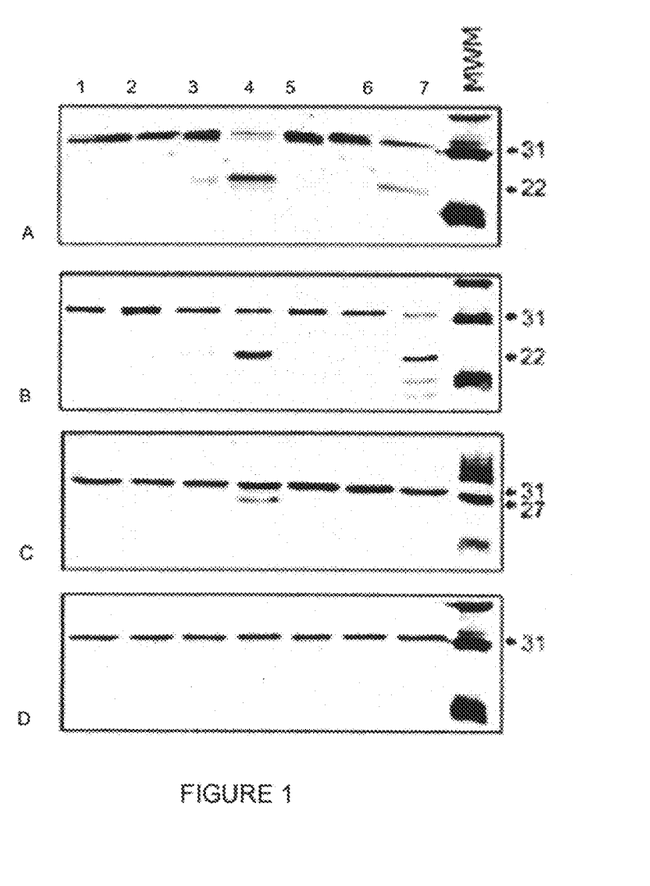
FIG. 1 shows cleavage of recombinant galectin-3 by MMP-2 and -9: One µg protein was incubated at 37° C. for the indicated time with activated or pro enzyme and separated on a 15% polyacrylamide gel.

Recombinant proteins were incubated with purified active MMP-2 or MMP-9 for 15 and 60 min respectively (FIG. 1). Wild type and A33G galectin-3 produced a polypeptide of ~22 kDa consistent with cleavage at $Ala^{62}$-$Tyr^{63}$. The H64P mutant produced a ~27-kDa polypeptide upon incubation with MMP-2 indicating that it is cleaved at $Gly^{32}$-$Ala^{33}$. MMP-9 did not cleave the H64P mutant. Double mutation at A33G and H64P showed complete resistance to cleavage by both MMP-2 and MMP-9. The cleavage products were not seen when galectin-3 was incubated alone or with pro-MMPs.

Example 3

Expression of Galectin-3 in the Mutant Clones

Figure 2A:
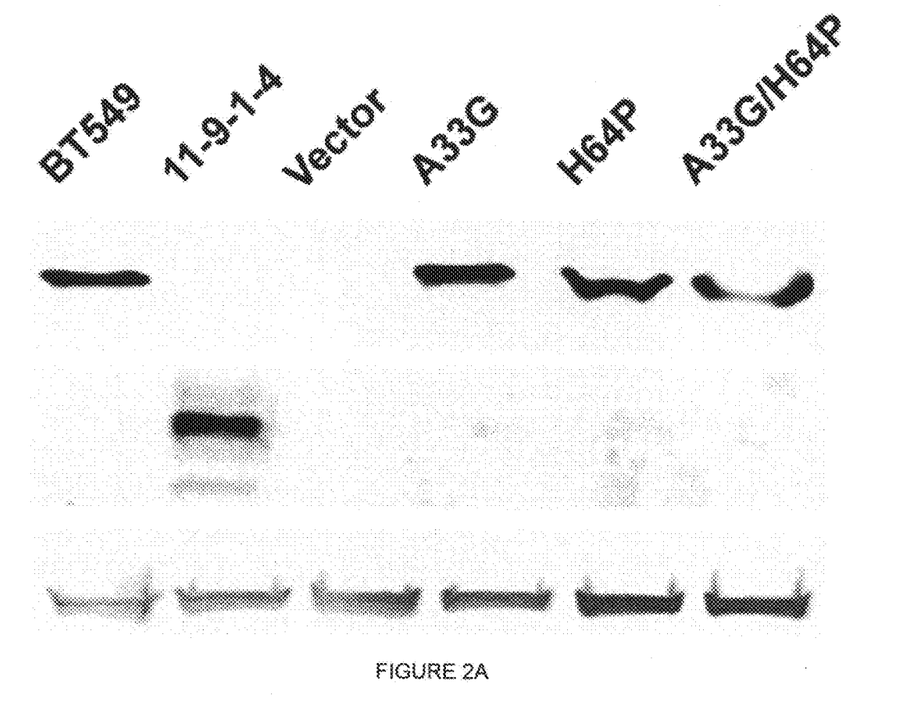
FIG. 2A shows expression of galectin-3 in BT-549 cell transfectants: I: Galectin-3 expression in total cell lysates. Fifty µg total protein was loaded per lane. II: Galectin-3 expression in the conditioned medium. 50 µg protein was loaded per lane. An additional band of ~27 kDa is present in 11-9-1-4. III: Actin was used as a loading control for cell lysate.

Galectin-3 was detected in the total cell lysates (FIG. 2AI) of all the BT-549 clones transfected with wild type and mutant galectin-3. Galectin-3 expression was also seen in the nucleus and cell surface. However, secretion of full length as well as the ~27-kDa polypeptide was detected only in 11-9-1-4 (FIG. 2AII).

Example 4

Figure 2B:
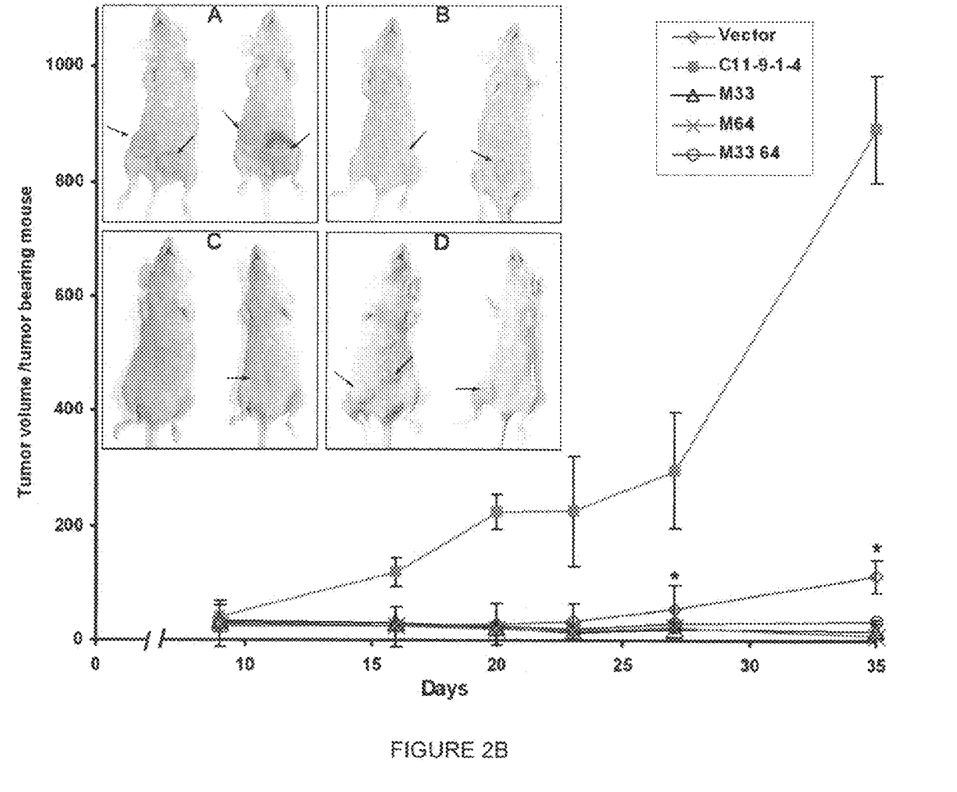
FIG. 2B shows tumorigenicity of various BT-549 transfected cell clones in nude mice: Each point is the average of the tumor volume in tumor bearing mice. The bars represent standard error. p values with respect to 11-9-1-4 on day 35 were 0.0071, 0.0036, 0.0036 and 0.0042 and on day 27 were 0.0099, 0.0048, 0.0050, and 0.0060 respectively for vector, M33, M64 and M33+64 respectively. Inset: pictures of representative mice at the time of sacrifice. Arrows indicate tumors.

Tumorigenicity of Mutant Clones $2 \times 10^6$ cells from each clone were injected in the mammary fat pad region of nude mice to study the effect of galectin-3 mutation on tumor take and growth. By 5 weeks there was ~60% tumor take in the wild type transfected cell clone (11-9-1-4) and only 10, 3, 6, and 23% in M33, M64, M33+64, and vector transfected cells respectively (average of two experiments). Average tumor volume in tumor bearing mice of the representative experiment through day 35 is depicted in FIG. 2B. Due to increased tumor burden, mice injected with 11-9-1-4 cells were sacrificed after 5 weeks, other groups were sacrificed after 8 weeks. The average tumor weight at the time of sacrifice in 11-9-1-4 was 1.7+/−1.44 gm and 0.7+/−0.07, 0.6+/−1.13, 0.05+/−0.03 and 0.5+/−0.98 gm with p values 0.020, 0.018, 0.0006 and 0.011 respectively for vector, M33, M64 and M33+64.

Example 5

Immunohistochemical Analysis of Xenografts

Figure 3:
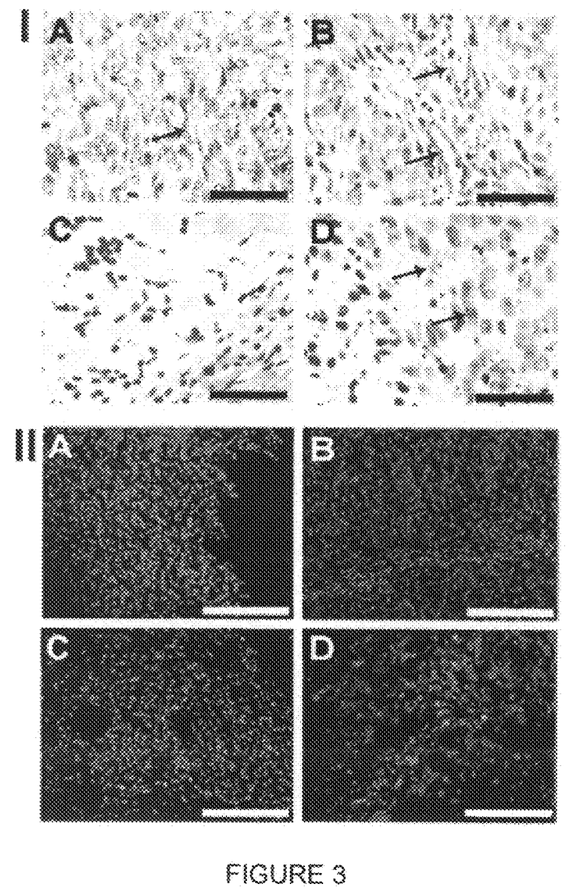

Tumor specimens were sectioned and stained with anti-CD34 antibody to visualize angiogenesis (FIG. 3A). The 5 week tumor of the 11-9-1-4 cell clone depicted many fully formed blood vessels with lumens (top right), whereas vector and M33+64 mutant cells' tumor of 8 weeks showed a few endothelial precursor cells (fibrocytes) that were positive for CD34, indicating the slow initiation of angiogenesis (top left and bottom right). No tumors could be obtained from M64 mutant cell clone. No blood vessels or precursor cells were seen in M33 xenograft even after 8 weeks (bottom left).

The xenografts obtained from vector alone, M33 and M33+64 mutant cell clones (FIG. 3B top left, bottom right and bottom left) showed a very high incidence of apoptosis using TUNEL assay, whereas no significant apoptosis could be detected in BT-549 wild type 11-9-1-4 tumors (FIG. 3B top left).

Example 6

Figure 4:
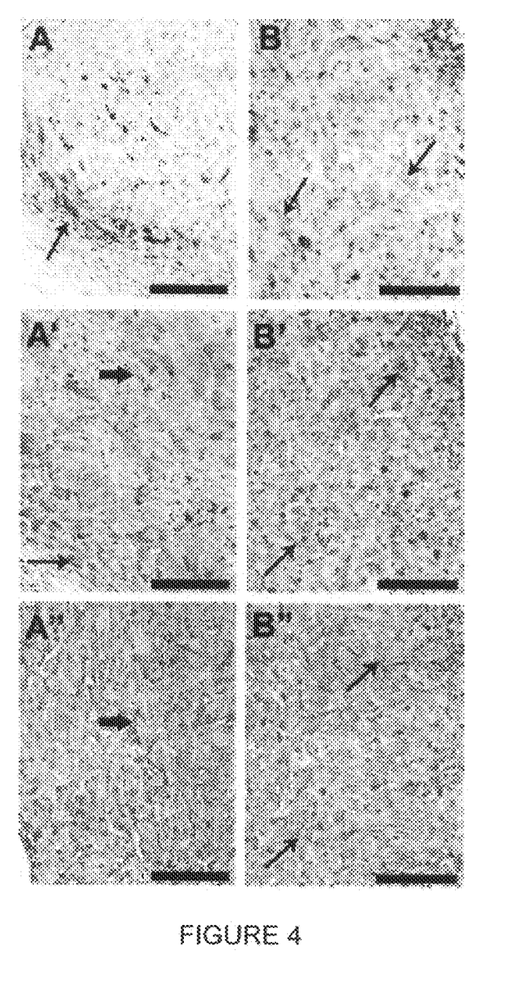
FIG. 4 shows distribution of full length and cleaved galectin-3 in the xenografts. Full length galectin-3 is localized on the peripheral cells of the 11-9-1-4 xenograft (arrow) (A), cleavage products are seen in peripheral (arrow) as well as luminal (wider arrow) cells of the section (A'). MMP-9 is localized more intensely in the luminal cells of the section (wider arrow) (A"), where cleaved form of galectin-3 is predominant. In M33+64, monoclonal (mAb) PBZ, polyclonal antibody (pAb) (B') as well as anti-MMP-9 (B") showed a more uniform distribution throughout the section. Bar: 100 micron.

Galectin-3 Cleavage as Surrogate Marker for MMP Activity in Tumor Xenografts Anti-MMP-2/9 and anti-galectin-3 monoclonal and polyclonal antibodies were used to visualize whether cleaved galectin-3 could be identified in the xenografts (FIG. 4). In 11-9-14 xenograft, full length galectin-3 (using monoclonal antibody) is present in tumor cells localized in the periphery of the tumor mass (arrow), whereas cleaved galectin-3 (using polyclonal antibody) as well as MMP-9 are localized in tumor cells present in the center of the xenograft (arrowheads). M33+64 xenograft, on the other hand did not show differences in the distribution of galectin-3 using either monoclonal or polyclonal antibody. Because the mutant galectin-3 is resistant to cleavage, there was no indication of its cleavage despite of the presence of MMP-9 throughout the section. MMP-2 also showed a staining pattern similar to MMP-9. Immuno-staining with mouse, rat and rabbit IgG as negative controls for MMP-2/-9, mono and polyclonal galectin-3 respectively did not show any staining.

Example 7

Figure 5:
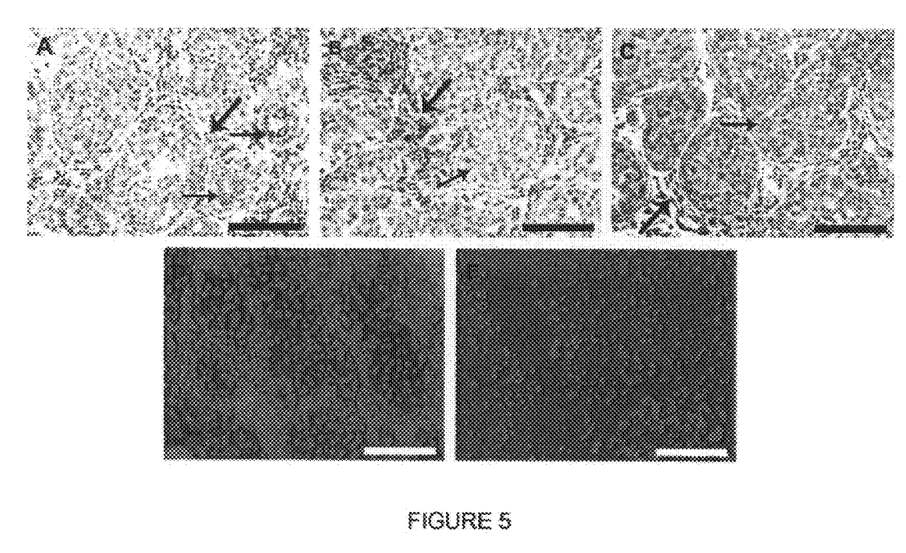
FIG. 5 shows distribution of full length and cleaved galectin-3 in MCF10 DCIS.com xenograft: A: paraffin embedded; B: fresh frozen. A: left: monoclonal anti galectin-3 antibody shows mainly epithelial and some stromal labeling (arrows); B middle: polyclonal anti-galectin-3 antibody shows some epithelial (arrow) and strong stromal labeling (wider arrows); C right: anti-MMP-9 antibody showing epithelial (arrow) and stromal (wider arrow) labeling. D left: In situ zymography in the fresh frozen section showing stromal activity (green color), nuclei were stained with DAPI (blue color); E right: In situ zymography in the presence of 20 mM EDTA. Bar: 100 micron.

Galectin-3 Cleavage as Surrogate Marker for MMP Activity in Ductal Carcinoma In Situ (DCIS) Xenografts and Human Breast Cancer Tissue In DCIS xenografts, intact galectin-3 was localized mainly in the cytoplasm of epithelial cells in focally intense clusters (FIG. 5 top left) as recognized by the monoclonal antibody. Some cells in the stroma also stained positive with this antibody (arrow). Cleaved galectin-3 (top right) and MMP-9 (bottom left) was distributed throughout the ducts and the stroma. In situ zymography on fresh frozen DCIS xenograft sections showed no gelatinolytic activity in the epithelial ducts, whereas positive activity was seen in the stroma (FIG. 5 bottom middle), which was abrogated when incubated with EDTA, a non-specific MMP inhibitor (bottom right).

Figure 6:
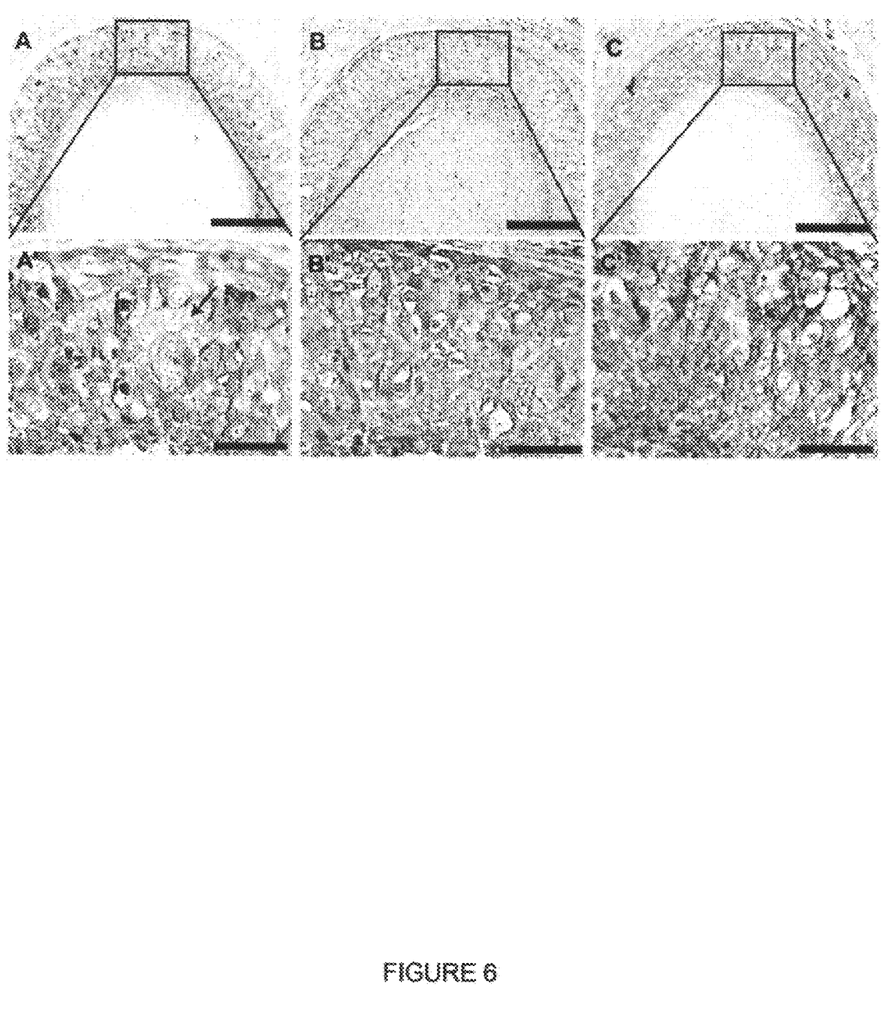
FIG. 6 shows distribution of full-length and cleaved galectin-3 in human breast cancer: A: DCIS; B: Infiltrating ductal carcinoma. In human DCIS (A), full-length galectin-3 is concentrated more towards the lumen of the duct, many cells towards the stromal end are devoid of the protein (mAb; arrow). The cleaved galectin-3 fragments (pAb) as well as MMP-9 could be seen in all cells. In infiltrating ductal carcinoma (B), full-length galectin-3 is seen in ductules that maintained a normal morphology (arrow) and in some invasive cells (mAb); cleaved galectin-3 (pAb) and MMP-9 (C) are seen in invasive cell clusters and stroma (arrows). Lower panels A', B' and C' represent the boxes in the upper A, B and C panels. Bar: 50 micron (upper panels); 200 micron (lower panels).

In the human DCIS, full-length galectin-3 was more intensely localized towards the luminal side, and many cells on the stromal side of the duct were devoid of the protein (FIG. 6A left). Cleaved protein (middle) and MMP-9 (right) were distributed uniformly in all the cells indicating that many cells adjacent to stroma have cleaved galectin-3 and active MMP-2 and -9. In the infiltrating ductal carcinoma the presence of full-length galectin-3 was seen in the ductules that still maintained a normal morphology (FIG. 6B left) and a positive reactivity for the cleaved galectin-3 in normal ductules as well in the invasive cells and stroma (middle). MMP-9, on the other hand, was not expressed in the normal ductules, but localized in the stroma and clusters of invasive cells (co-localizing with the cleaved galectin-3) (right) implying that it was in the active form.

REFERENCES CITED (1) Nelson A R, Fingleton B, Rothenberg M L, Matrisian L M. Matrix metalloproteinases: biologic activity and clinical implications. J Clin Oncol 2000; 18:1135-49.

(2) Itoh T, Tanioka M, Yoshida H, Yoshioka T, Nishimoto H, Itohara S. Reduced angiogenesis and tumor progression in gelatinase A-deficient mice. Cancer Res 1998; 58:1048-51.

(3) Bergers G, Brekken R, McMahon G, et al. Matrix metalloproteinase-9 triggers the angiogenic switch during carcinogenesis. Nat Cell Biol 2000; 2:737-44.

(4) Lindsey M L. Novel strategies to delineate matrix metalloproteinase (MMP)-substrate relationships and identify targets to block MMP activity. Mini Rev Med Chem 2006; 6:1243-8.

(5) Zucker S, Cao J, Chen W T. Critical appraisal of the use of matrix metalloproteinase inhibitors in cancer treatment. Oncogene 2000; 19:6642-50.

(6) Chantrain C F, Shimada H, Jodele S, et al. Stromal matrix metalloproteinase-9 regulates the vascular architecture in neuroblastoma by promoting pericyte recruitment. Cancer Res 2004; 64:1675-86.

(7) Kalluri R. Basement membranes: structure, assembly and role in tumour angiogenesis. Nat Rev Cancer 2003; 3:422-33.

(8) Xu J, Rodriguez D, Petitclerc E, et al. Proteolytic exposure of a cryptic site within collagen type IV is required for angiogenesis and tumor growth in vivo. J Cell Biol 2001; 154:1069-79.

(9) Deryugina E I, Soroceanu L, Strongin A Y. Up-regulation of vascular endothelial growth factor by membrane-type 1 matrix metalloproteinase stimulates human glioma xenograft growth and angiogenesis. Cancer Res 2002; 62:580-8.

(10) Herren B, Levkau B, Raines E W, Ross R. Cleavage of beta-catenin and plakoglobin and shedding of VE-cadherin during endothelial apoptosis: evidence for a role for caspases and metalloproteinases. Mol Biol Cell 1998; 9:1589-601.

(11) Patterson B C, Sang Q A. Angiostatin-converting enzyme activities of human matrilysin (MMP-7) and gelatinase B/type IV collagenase (MMP-9). J Biol Chem 1997; 272:28823-5.

(12) Dong Z, Kumar R, Yang X, Fidler I J. Macrophage-derived metalloelastase is responsible for the generation of angiostatin in Lewis lung carcinoma. Cell 1997; 88:801-10.

(13) Nagase H, Woessner J F, Jr. Matrix metalloproteinases. J Biol Chem 1999; 274:21491-4.

(14) Van de Wiele C, Oltenfreiter R. Imaging probes targeting matrix metalloproteinases. Cancer Biother Radiopharm 2006; 21:409-17.

(15) Chiappori A A, Eckhardt S G, Bukowski R, et al. A phase I pharmacokinetic and pharmacodynamic study of s-3304, a novel matrix metalloproteinase inhibitor, in patients with advanced and refractory solid tumors. Clin Cancer Res 2007; 13:2091-9.

(16) Wright J L, Tai H, Wang R, Wang X, Churg A. Cigarette smoke upregulates pulmonary vascular matrix metalloproteinases via TNF-alpha signaling. Am J Physiol Lung Cell Mol Physiol 2007; 292:L125-33.

(17) Stuelten C H, DaCosta Byfield S, Arany P R, Karpova T S, Stetler-Stevenson W G, Roberts A B. Breast cancer cells induce stromal fibroblasts to express MMP-9 via secretion of TNF-alpha and TGF-beta. J Cell Sci 2005; 118:2143-53.

(18) Barondes S H, Cooper D N, Gitt M A, Leffler H. Galectins. Structure and function of a large family of animal lectins. J Biol Chem 1994; 269:20807-10.

(19) Ochieng J, Fridman R, Nangia-Makker P, et al. Galectin-3 is a novel substrate for human matrix metalloproteinases-2 and -9. Biochemistry 1994; 33:14109-14.

(20) Gong H C, Honjo Y, Nangia-Makker P, et al. The NH2 terminus of galectin-3 governs cellular compartmentalization and functions in cancer cells. Cancer Res 1999; 59:6239-45.

(21) Dumic J, Dabelic S, Flogel M. Galectin-3: an open-ended story. Biochim Biophys Acta 2006; 1760:616-35.

(22) Nangia-Makker P, Akahani S, Bresalier R, Raz A. The role of Galectin-3 in tumor metastasis. In: Caron M, Seve A-P, editors. Lectins and Pathology. New Jersey: Harwood Academic Publishers; 2000. p. 67-77.

(23) Shekhar M P, Nangia-Makker P, Tait L, Miller F, Raz A. Alterations in galectin-3 expression and distribution correlate with breast cancer progression: functional analysis of galectin-3 in breast epithelial-endothelial interactions. Am J Pathol 2004; 165:1931-41.

(24) Nangia-Makker P, Thompson E, Hogan C, Ochieng J, Raz A. Induction of tumorigenicity by galectin-3 in a non-tumorigenic human breast carcinoma cell line. Int J Oncol 1995; 7:1079-87.

(25) Miller F R, Santner S J, Tait L, Dawson P J. MCF10DCIS.com xenograft model of human comedo ductal carcinoma in situ. J Natl Cancer Inst 2000; 92:1185-6.

(26) Ochieng J, Green B, Evans S, James O, Warfield P. Modulation of the biological functions of galectin-3 by matrix metalloproteinases. Biochim Biophys Acta 1998; 1379:97-106.

(27) Olson M W, Gervasi D C, Mobashery S, Fridman R. Kinetic analysis of the binding of human matrix metalloproteinase-2 and -9 to tissue inhibitor of metalloproteinase (TIMP)-1 and TIMP-2. J Biol Chem 1997; 272:29975-83.

(28) Tait L R, Pauley R J, Santner S J, et al. Dynamic stromal-epithelial interactions during progression of MCF10DCIS.com xenografts. Int J Cancer 2007; 120:2127-34.

(29) Mook O R, Van Overbeek C, Ackema E G, Van Maldegem F, Frederiks W M. In situ localization of gelatinolytic activity in the extracellular matrix of metastases of colon cancer in rat liver using quenched fluorogenic DQ-gelatin. J Histochem Cytochem 2003; 51:821-9.

(30) Overall C M, Lopez-Otin C. Strategies for MMP inhibition in cancer: innovations for the post-trial era. Nat Rev Cancer 2002; 2:657-72.

(31) Coussens L M, Fingleton B, Matrisian L M. Matrix metalloproteinase inhibitors and cancer: trials and tribulations. Science 2002; 295:2387-92.

(32) Opdenakker G, Van den Steen P E, Van Damme J. Gelatinase B: a tuner and amplifier of immune functions. Trends Immunol 2001; 22:571-9.

(33) Levi E, Fridman R, Miao H Q, Ma Y S, Yayon A, Vlodavsky I. Matrix metalloproteinase 2 releases active soluble ectodomain of fibroblast growth factor receptor 1. Proc Natl Acad Sci USA 1996; 93:7069-74.
(34) Schenk S, Hintermann E, Bilban M, et al. Binding to EGF receptor of a laminin-5 EGF-like fragment liberated during MMP-dependent mammary gland involution. J Cell Biol 2003; 161:197-209.
(35) Pirila E, Sharabi A, Salo T, et al. Matrix metalloproteinases process the laminin-5 gamma 2-chain and regulate epithelial cell migration. Biochem Biophys Res Commun 2003; 303:1012-7.
(36) Handsley M M, Edwards D R. Metalloproteinases and their inhibitors in tumor angiogenesis. Int J Cancer 2005; 115:849-60.
(37) John C M, Leffler H, Kahl-Knutsson B, Svensson I, Jarvis G A. Truncated galectin-3 inhibits tumor growth and metastasis in orthotopic nude mouse model of human breast cancer. Clin Cancer Res 2003; 9:2374-83.
(38) Yang R Y, Hsu D K, Liu F T. Expression of galectin-3 modulates T-cell growth and apoptosis. Proc Natl Acad Sci USA 1996; 93:6737-42.
(39) Dagher S F, Wang J L, Patterson R J. Identification of galectin-3 as a factor in pre-mRNA splicing. Proc Natl Acad Sci USA 1995; 92:1213-7.
(40) Akahani S, Nangia-Makker P, Inohara H, Kim H R, Raz A. Galectin-3: a novel antiapoptotic molecule with a functional BH1 (NWGR) domain of Bcl-2 family. Cancer Res 1997; 57:5272-6.
(41) Liu F T, Patterson R J, Wang J L. Intracellular functions of galectins. Biochim Biophys Acta 2002; 1572:263-73.
(42) Liu F T, Frigeri L G, Gritzmacher C A, Hsu D K, Robertson M W, Zuberi R I. Expression and function of an IgE-binding animal lectin (epsilon BP) in mast cells. Immunopharmacology 1993; 26:187-95.
(43) Hughes R C. The galectin family of mammalian carbohydrate-binding molecules. Biochem Soc Trans 1997; 25:1194-8.
(44) Perillo N L, Uittenbogaart C H, Nguyen J T, Baum L G. Galectin-1, an endogenous lectin produced by thymic epithelial cells, induces apoptosis of human thymocytes. J Exp Med 1997; 185:1851-8.
(45) Rabinovich G A, Riera C M, Landa C A, Sotomayor C E. Galectins: a key intersection between glycobiology and immunology. Braz J Med Biol Res 1999; 32:383-93.
(46) Nangia-Makker P, Baccarini S, Raz A. Carbohydrate-recognition and angiogenesis. Cancer and Metastasis Reviews 2000; 19:51-7.
(47) Ochieng J, Leite-Browning M L, Warfield P. Regulation of cellular adhesion to extracellular matrix proteins by galectin-3. Biochem Biophys Res Commun 1998; 246:788-91.
(48) Honjo Y, Nangia-Makker P, Inohara H, Raz A. Down regulation of galectin-3 suppresses tumorigenicity of human breast carcinoma cells. Clin Cancer Res 2001; 7:661-8.
(49) Bresalier R S, Mazurek N, Sternberg L R, et al. Metastasis of human colon cancer is altered by modifying expression of the beta-galactoside-binding protein galectin 3. Gastroenterology 1998; 115:287-96.
(50) Nangia-Makker P, Honjo Y, Sarvis R, et al. Galectin-3 induces endothelial cell morphogenesis and angiogenesis. Am J Pathol 2000; 156:899-909.

While the description above refers to particular embodiments of the present invention, it will be understood that many modifications may be made without departing from the spirit thereof. The presently disclosed embodiments are therefore to be considered in all respects as illustrative and not restrictive. All patents, patent applications, provisional applications, and publications referred to or cited herein are incorporated by reference in their entirety, including all figures and tables, to the extent they are not inconsistent with the explicit teachings of this specification.

We claim:

1. A method of detecting matrix metalloproteinase (MMP) activity in a biological tissue sample comprising detecting native full-length and cleaved galectin-3 in said sample by contacting said sample with at least one anti-galectin-3 antibody that binds full-length galectin-3 and at least one antibody that binds cleaved galectin-3, determining the binding of said antibodies in said sample, wherein the presence of cleaved galectin-3 binding to said antibody correlates with the presence of MMP-2 or MMP-9 enzymatic activity in said sample; and confirming the presence of MMP within said sample by contacting said sample with at least one antibody capable of recognizing at least one of MMP-2 and MMP-9 and detecting binding of said antibody to said MMP.

2. The method of claim 1 wherein said biological tissue sample contains tumor cells.

3. The method of claim 1, wherein said antibody to full-length galectin-3 is produced by clone TIB166.

4. The method of claim 1, wherein said antibody to cleaved galectin-3 is anti-hL31.

5. The method of claim 1, wherein said sample is paraffin-embedded or fresh frozen, and analyzed using immunohistochemical analysis.

6. A method for evaluating the progress of ductal carcinoma in situ, said method comprising obtaining a tissue sample from a patient being screened for ductal carcinoma, contacting said sample with an antibody to full length galectin-3 and an antibody to cleaved galectin-3, imaging the binding of said antibodies in said sample, contacting said sample with an antibody that binds MMP-9 and detecting binding of said antibody in said sample wherein MMP-9 binding corresponds to the presence of invasive cells.

* * * * *

```
SEQUENCE LISTING

<160> NUMBER OF SEQ ID NOS: 4

<210> SEQ ID NO 1
<211> LENGTH: 25
<212> TYPE: DNA
<213> ORGANISM: Human

<400> SEQUENCE: 1
ctgctggggg aggggctac ccagg                                             25

<210> SEQ ID NO 2
<211> LENGTH: 25
<212> TYPE: DNA
<213> ORGANISM: human

<400> SEQUENCE: 2
cctgggtagc ccctccccc agcag                                             25

<210> SEQ ID NO 3
<211> LENGTH: 25
<212> TYPE: DNA
<213> ORGANISM: human

<400> SEQUENCE: 3
gcgcctaccc tggagcacct ggagc                                            25
```

```
<210> SEQ ID NO 4
<211> LENGTH: 25
<212> TYPE: DNA
<213> ORGANISM: human

<400> SEQUENCE: 4
gctccaggtg ctccagggta ggcgc                                              25
```